United States Patent
Kaji et al.

(10) Patent No.: US 6,716,300 B2
(45) Date of Patent: Apr. 6, 2004

(54) EMISSION SPECTROSCOPIC PROCESSING APPARATUS

(75) Inventors: Tetsunori Kaji, Tokuyama (JP); Shizuaki Kimura, Kudamatsu (JP); Tatehito Usui, Chiyoda (JP); Takashi Fujii, Coppell, TX (US)

(73) Assignees: Hitachi, Ltd., Tokyo (JP); Hitachi High-Technologies Corporation, Tokyo (JP)

( * ) Notice: Subject to any disclaimer, the term of this patent is extended or adjusted under 35 U.S.C. 154(b) by 99 days.

(21) Appl. No.: 10/090,759

(22) Filed: Mar. 6, 2002

(65) Prior Publication Data

US 2003/0098290 A1 May 29, 2003

(30) Foreign Application Priority Data

Nov. 29, 2001  (JP) ......................................... 2001-364626

(51) Int. Cl.[7] ............................. H05H 1/00; C23C 16/00
(52) U.S. Cl. ............................. 156/345.24; 156/345.25; 118/712
(58) Field of Search ........................ 156/345.24, 345.25, 156/345.26, 345.27, 345.28; 118/712, 713, 715

(56) References Cited

U.S. PATENT DOCUMENTS

| | | | | | |
|---|---|---|---|---|---|
| 6,306,669 | B1 | * | 10/2001 | Yano et al. ................... | 438/14 |
| 6,383,402 | B1 | * | 5/2002 | Smith et al. .................. | 216/60 |
| 6,414,499 | B2 | * | 7/2002 | Yano et al. .................. | 324/753 |
| 2003/0085198 | A1 | * | 5/2003 | Yi et al. ........................ | 216/60 |

* cited by examiner

*Primary Examiner*—Parviz Hassanzadeh
(74) *Attorney, Agent, or Firm*—Antonelli, Terry, Stout & Kraus, LLP

(57) ABSTRACT

An emission spectroscopic processing apparatus includes a spectroscope for spectrally separating input light emitted from a process unit into component spectra, a light receiving unit including a series of light receiving elements for detecting light quantities of the component spectra on a wavelength basis, a first signal hold unit for holding sequentially each of detection signals outputted from a subset of adjacent light receiving elements contained in series of light receiving elements during a first period, an adder unit for adding together the detection signals of adjacent light receiving elements of the light receiving unit inclusive of the held detection signals of the subset of adjacent light receiving elements, a second signal hold unit for holding sequentially sum outputs of the adder unit, and a signal processing unit for determining a state of the process unit on the basis of the output of the second signal hold unit.

5 Claims, 11 Drawing Sheets

EMISSION SPECTROSCOPIC PROCESSING APPARATUS

CROSS-REFERENCE TO RELATED APPLICATION

The present invention is related to (1) U.S. patent application Ser. No. 09/793,624 filed Feb. 27, 2001, (2) U.S. patent application Ser. No. 09/797,601 filed Mar. 5, 2001 and (3) U.S. patent application Ser. No. 09/946,504 filed Sep. 6, 2001.

BACKGROUND OF THE INVENTION

The present invention relates generally to an emission spectroscopic processing apparatus for spectrally separating radiation emitted from a plasma or the like into component spectra, converting the component spectra having respective wavelengths into electric signals by means of associated light receiving elements, respectively, and obtaining a desired detection output by processing the signals. Further, the present invention relates to a plasma processing method using the emission spectroscopic processing apparatus.

The emission spectroscopic processing apparatus for spectrally separating radiation emitted from a plasma or the like into component spectra, converting the component spectra having respective wavelengths into electric signals by means of light receiving elements or devices and obtaining a desired detection output by processing the signals has been known heretofore. By way of example, a process monitoring apparatus adopting a main component analysis process mentioned below is disclosed, for example, in European Patent No. 1089146.

More specifically, electromagnetic radiation emitted from a plasma camber is inputted into a process monitoring apparatus which is composed of a spectrometer and a processor through the medium of an optical fiber or the like. The spectrometer mentioned above is designed to spatially split or separate the electromagnetic radiation of plasma on the basis of the wavelengths by using, for example, a prism or a diffraction grating. Subsequently, a plurality of spatially separated spectra of respective wavelengths are detected by means of e.g. a CCD (Charge Coupled Device) array of 2048 channels, whereby a detection signal, i.e., OES (Optical Emission Spectroscopic) signal is generated. The OES signal is then digitized through e.g. an analogue-to-digital (A/D converter) to be outputted to a processor for undergoing further processings. In this manner, the electromagnetic radiation emitted from a plasma is measured by the spectrometer and supplied to the processor in the form of the OES signal of 2048 channels.

Main or major component analysis process of a specific or desired type to be executed by the processor is selected by means of a remote computer system, fabrication equipment or the like. In place of the spectrometer, there may be employed a diffraction grating, prism, optical filter or other type of wavelength selecting device(s) in combination with a plurality of detectors (e.g. photodiodes, photo multipliers or the like) to thereby supply the information concerning a plurality of electromagnetic radiation wavelengths to the processor. In this conjunction, it is to be added that the processor is coupled to a plasma etching controller by way of a control bus.

SUMMARY OF THE INVENTION

In practice, the CCD array is used in many applications as the convenient means for making available radiation amplitude signals corresponding to the wavelengths of the component spectra. However, in the CCD array which is constituted by a large number of integrated light receiving elements, such a problem is encountered that when the light receiving elements each of small capacity are employed in an effort to increase the sensitivity, then noise also increases, whereas when the light receiving elements of large capacity are employed with a view to suppressing the noise, the sensitivity of the CCD array will become lowered. By way of example, in the case of a CCD array of a relatively high sensitivity (e.g. 2048-pixel CCD linear sensor "ILX511" commercially availably from Sony Co. Ltd), the signal-to-noise ratio (S/N ratio) is on the order of 250 in the state where a quantity of light of saturation level is received, and the S/N ratio decreases in proportion to the one-second power (½) of the received light quantity as it deceases. This problem is not inherent to the CCD array but generally common to photosensor devices each composed of a large number of integrated light receiving elements.

In the ordinary image sensor, a mean value of the received light quantity distribution over the whole image or a peak value thereof is measured for the purpose of effectuating a gain adjustment for changing the amplification factor for the output signal of the CCD array or the charge storing time thereof on the basis of the measured value in order to cope with changes or variations in the quantity of incident light or radiation. In this conjunction, reference may be made to, for example, Japanese Patent Application Laid-Open Publication No. 324297/2000 and USP 2001/0016053A1.

On the other hand, in the plasma processing apparatus, the incident radiation quantity may change remarkably (ca. ten times or more) due to aged contamination of a process chamber. For coping with such change of the incident radiation quantity, it is not preferred to change the charge storing time of the CCD array because then the operation timing of the whole system will have to be changed remarkably. Further, in the spectrum of plasma emission produced in the plasma processing apparatus, there are coexistent mixedly a plurality of high luminance portions exhibiting steep peaks and low luminance portions changing relatively gently as a function of the wavelength (see e.g. U.S. Pat. No. 6,261,470B1, FIG. 17A or European Patent No. 1089146, FIG. 3C). In the applications where the emission spectra are detected by using the CCD array, setting of the amplification factor for the output signal of the CCD array so that no saturation can occur at the steep peaks will inevitably be accompanied with remarkable degradation of the S/N ratio for the low luminance portion of the radiation. On the contrary, when the amplification factor is set in conformance with the low luminance portion, saturation will easily occur in the peak portions.

In a semiconductor fabrication apparatus, the time-dependent changes of emission spectra emitted from a process chamber of the apparatus (i.e., change of the emission spectra in the course of times lapse) indicate changes in the contents of processing or treatment being carried out within the chamber. In recent years, it has been practiced to estimate the process situation or statuses within the process chamber on the basis of extremely small or minute changes of the emission spectra. However, in the case where the CCD array or the like device is used as the means for detecting the emission spectra, the signal which can be made available is very poor in respect to the S/N ratio as mentioned previously. Such being the circumstances, addition of the signal of a same wavelength is repeated a number of times in an effort to eliminate the noise components. However, with this method, it is necessary to repetitively perform the addition of a sample one hundred times or more if the signal-to-noise ratio is to be increased by one order of magnitude. Such processing will ordinarily require several to several ten seconds, which in turn renders it relatively difficult to detect the minute change (change of less than 10% or so) of high rate or speed on the order of one second or 0.5 second or lower in terms of temporal duration. In particular, in a low luminance portion which changes relatively gently as a function of the wavelength in the emission spectra such as of plasma, great difficulty will be encountered in detecting the minute change of high rate on the order of one second or less with satisfactory reproducibility.

In the light of the state of the art described above, it is an object of the present invention to provide an emission spectroscopic processing apparatus which is capable of detecting minute changes in emission spectra of high rate or speed on the order of one second or less with enhanced or improved reproducibility.

Another object of the present invention is to provide a plasma processing method which is carried out by using the emission spectroscopic processing apparatus mentioned above.

In view of the above and other objects which will become apparent as the description proceeds, there is provided according to an aspect of the present invention an emission spectroscopic processing apparatus which includes a spectroscope for spectrally separating input light emitted from a process unit into component spectra, a light receiving unit including a series of light receiving elements for detecting light quantities of the component spectra on a wavelength-by-wavelength basis, a first signal hold circuit for holding sequentially each of detection signals outputted from subsets of adjacent light receiving elements contained in said series of light receiving elements for a first period, respectively, an adder unit for adding together the detection signals of adjacent light receiving elements of the light receiving unit inclusive of the held detection signals of the subset of the adjacent light receiving elements, a second signal hold unit for holding sequentially sum outputs of the adder unit, and a signal processing unit for determining a state of the process unit on the basis of the output of the second signal hold unit.

In a preferred mode for carrying out the invention, the emission spectroscopic processing apparatus includes a light receiving unit comprised of a series of light receiving elements for detecting light quantities of the component spectra on a wavelength-by-wavelength basis, an adder unit for adding together the detection signals outputted from light receiving elements which correspond to a set of emission wavelengths intrinsic to preset light emission materials, respectively, a third signal hold unit for holding sequentially sum outputs of the adder unit, and a signal process unit for determining a state of the processing unit on the basis of the output of the third signal hold unit.

Other objects, features and advantages of the invention will become apparent from the following description of the embodiments of the invention taken in conjunction with the accompanying drawings.

BRIEF DESCRIPTION OF THE DRAWINGS

In the course of the description which follows, reference is made to the drawings, in which.

DESCRIPTION OF THE EMBODIMENTS

Figure 1:
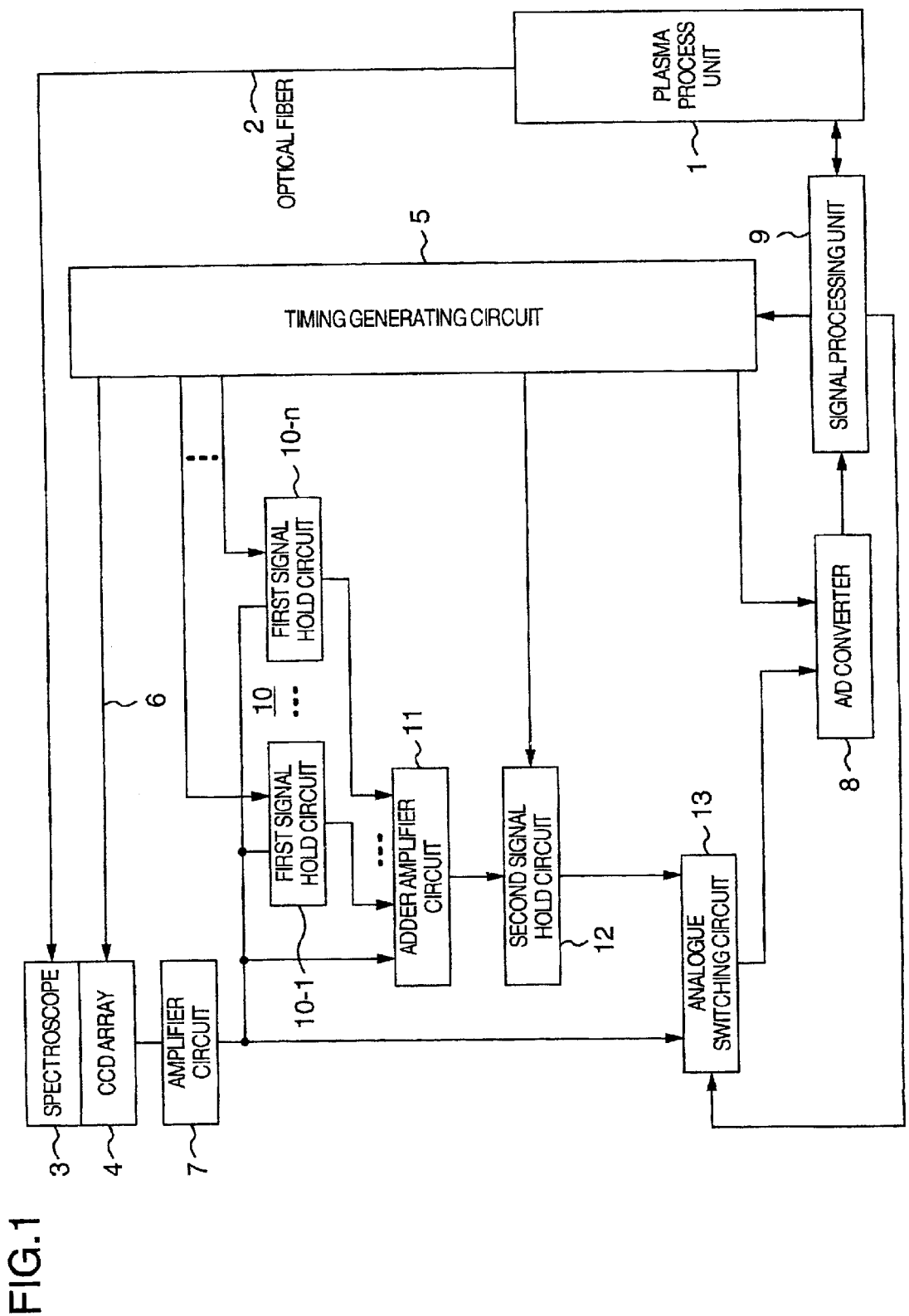
FIG. 1 is a block diagram showing schematically and generally a structure of an emission spectroscopic processing apparatus according to an embodiment of the present invention.

The present invention will be described in detail in conjunction with what is presently considered as preferred or typical embodiments thereof by reference to the drawings. In the following description, like reference characters designate like or corresponding parts throughout the several views.

FIG. 1 is a block diagram showing schematically and generally a structure of the emission spectroscopic processing apparatus according to an embodiment of the present invention. Referring to the figure, plasma emission produced within a treatment or process chamber of a plasma process unit 1 is introduced as input light into a spectroscope 3 through the medium of an optical fiber 2 via a slit. The spectroscope 3 serves for spectrally separating the input light passed through the slit into component spectra covering angles mutually differing on a wavelength-by-wavelength basis. The component spectra resulting from the spectral separation mentioned above then impinge onto a CCD (Charge Coupled Device) array 4 which incorporates an array or series of plural light receiving elements (ordinarily in a number ranging from several hundreds to several thousands, being however presumed in the following description that the number of the light receiving elements is 2048, only by way of example). Thus, a specific light receiving element (detecting element) disposed at a predetermined position in the CCD array or device 4 is capable of detecting the spectral intensity of a specific wavelength component of the incident radiation or light.

A timing generating circuit 5 is designed for generating a CCD reset timing signal and a CCD transfer clock signal. The CCD reset timing signal is effective for determining a storage time of electric charges stored in the CCD array, while the CCD transfer clock signal determines a transfer rate of time-serial signals outputted in time series from the CCD array 4. In the description which follows, both the signals mentioned above will collectively be referred to as the CCD drive signal 6, only for the convenience of description. Thus, the CCD array 4 is driven by the CCD drive signal 6, as a result of which plasma emission spectral wavelength distribution is outputted as the time-serial signal from the CCD array 4 periodically at a predetermined time interval. In succession, the time-serial signal is inputted to an amplifier circuit 7 which is imparted with an offset adjusting function and a gain adjusting function. At this juncture, it should be mentioned that in the case of the conventional emission spectroscopic processing apparatus known heretofore, the output of the amplifier circuit 7 is directly inputted to a signal processing unit 9 constituted by a CPU (Central Processing Unit) and others via an analogue-to-digital converter (hereinafter referred to as the A/D converter), whereby the wavelength distribution of the input light, time-dependent changes of light intensity at predetermined wavelengths and others are displayed on displaying devices incorporated in the signal processing unit 9.

By contrast, in the case of the emission spectroscopic processing apparatus according to the instant embodiment of the present invention now under consideration, the time-serial output signals delivered from the amplifier circuit 7 (as obtained by operating sequentially and repetitively the adjacent CCDs are stored in a plurality n of first signal hold circuits 10 (where n≧2) at different timings. The outputs from the plurality of first signal hold circuits 10 and that of the amplifier circuit 7 are added together by means of an adder amplifier circuit 11 the output of which is transferred to a second signal hold circuit 12 at a predetermined timing. In this manner, a plurality of signals corresponding to a plurality of different adjacent timings (i.e., a plurality of different adjacent wavelengths) are added together, to be outputted from the second signal hold circuit 12. The output signal from the second signal hold circuit 12 is then converted into a digital signal by means of the A/D converter 8 to be subsequently inputted to the signal processing unit 9.

In this way, by adding together the (n+1) signals (where n represents the number of the first signal hold circuits) by means of the first adder amplifier circuit 11, the S/N ratio of the output signal of the CCD array 4 can be improved by a factor of $\sqrt{n+1}$ while the amount of data inputted to the A/D converter 8 can be decreased by $1/(n+1)$. By performing this addition processing sequentially for the adjacent CCDs (i.e., for each of (n+1) adjacent CCDs), influence of noise inputted to the signal processing unit 9 can significantly be reduced or suppressed.

More specifically, in the case where the number n of the first signal hold circuits 10 is "8", the signal-to-noise ratio (i.e., S/N ratio) is improved by a factor of ca. "3" (i.e., three times). Similarly, when the number n of the first signal hold circuits 10 is "16", the S/N ratio is then improved by a factor of ca. "4". Further, when the number n of the first signal hold circuits 10 is "32", the S/N ratio can be improved approximately by a factor of "6". In this conjunction, it should be mentioned that an integrated circuit of a standard size in which eight signal processing circuits are integrated has already been commercially available. Accordingly, the size of the circuit portion comprised of the first signal hold circuits provides no serious problems in practical applications.

At this juncture, it is to be noted that since the data quantity is decreased through the analogue addition processing performed by the adder amplifier circuit 11 mentioned above, some difficulty will be encountered in analyzing the incident radiation with a high resolution (high wavelength resolution) without taking some appropriate measures.

For coping with the problem mentioned above, in the emission spectroscopic processing apparatus now under consideration, such arrangement can be adopted that when high resolution (wavelength resolution) is required,) the output of the amplifier circuit 7 and that of the second signal hold circuit 12 mentioned above are inputted to an analogue switch circuit 13. Thus, when the analysis of high resolution (wavelength resolution) is required, the analogue switch circuit 13 is changed over to the position for receiving the output of the amplifier circuit 7 in response to a command issued from the signal processing unit 9 so that the output of the amplifier circuit 7 can directly be inputted to the signal processing unit 9 by way of the AD (Analogue-to-Digital) converter 8. By virtue of this arrangement, it is possible to changeover with a single means (the analogue switch circuit 13) the mode in which the S/N ratio (resolution) is high with the wavelength resolution being relatively low on one hand and the mode in which the wavelength resolution is high with the S/N ratio being relatively low on the other hand.

Figure 2:
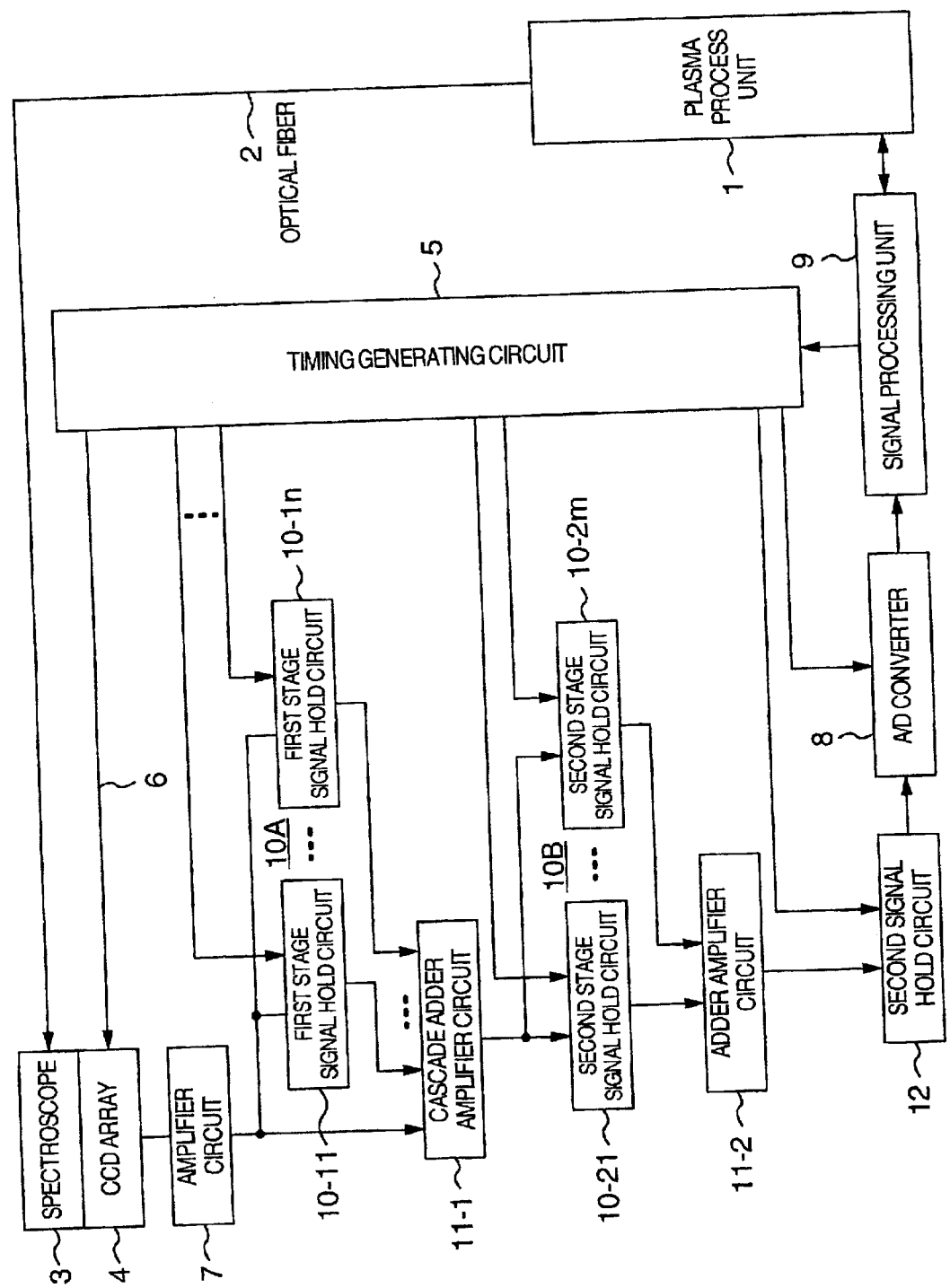
FIG. 2 is a block diagram showing schematically and generally a structure of an emission spectroscopic processing apparatus according to another embodiment of the present invention.

FIG. 2 is a block diagram showing schematically and generally a structure of the emission spectroscopic processing apparatus according to another embodiment of the present invention. The emission spectroscopic processing apparatus now under consideration primarily differs from that shown in FIG. 1 in the respect that the circuit portion corresponding to the first signal hold circuit generally denoted by 10 in the apparatus shown in FIG. 1 is replaced by a cascade connection in which a first stage signal hold circuit generally denoted by 10A including n (n≧2) signal hold circuits (10-11 to 10-1n) and a second stage signal hold circuit generally denoted by 10B including m (m≧2) signal hold circuits (10-21 to 10-2m) are connected in cascade through the medium of an interposed adder amplifier circuit 11-1. With this circuit arrangement, it is possible to improve the S/N ratio by a factor of $[(n+1)*(m+1)]^{1/2}$ with a relatively small number (n+m) of the signal hold circuits (10-11, . . . , 10-2n). By way of example, in the case where n=8 with m=8, the S/N ratio can be improved approximately by a factor of "9" (i.e., the S/N ratio can be improved about as high as nine times).

Figure 3:
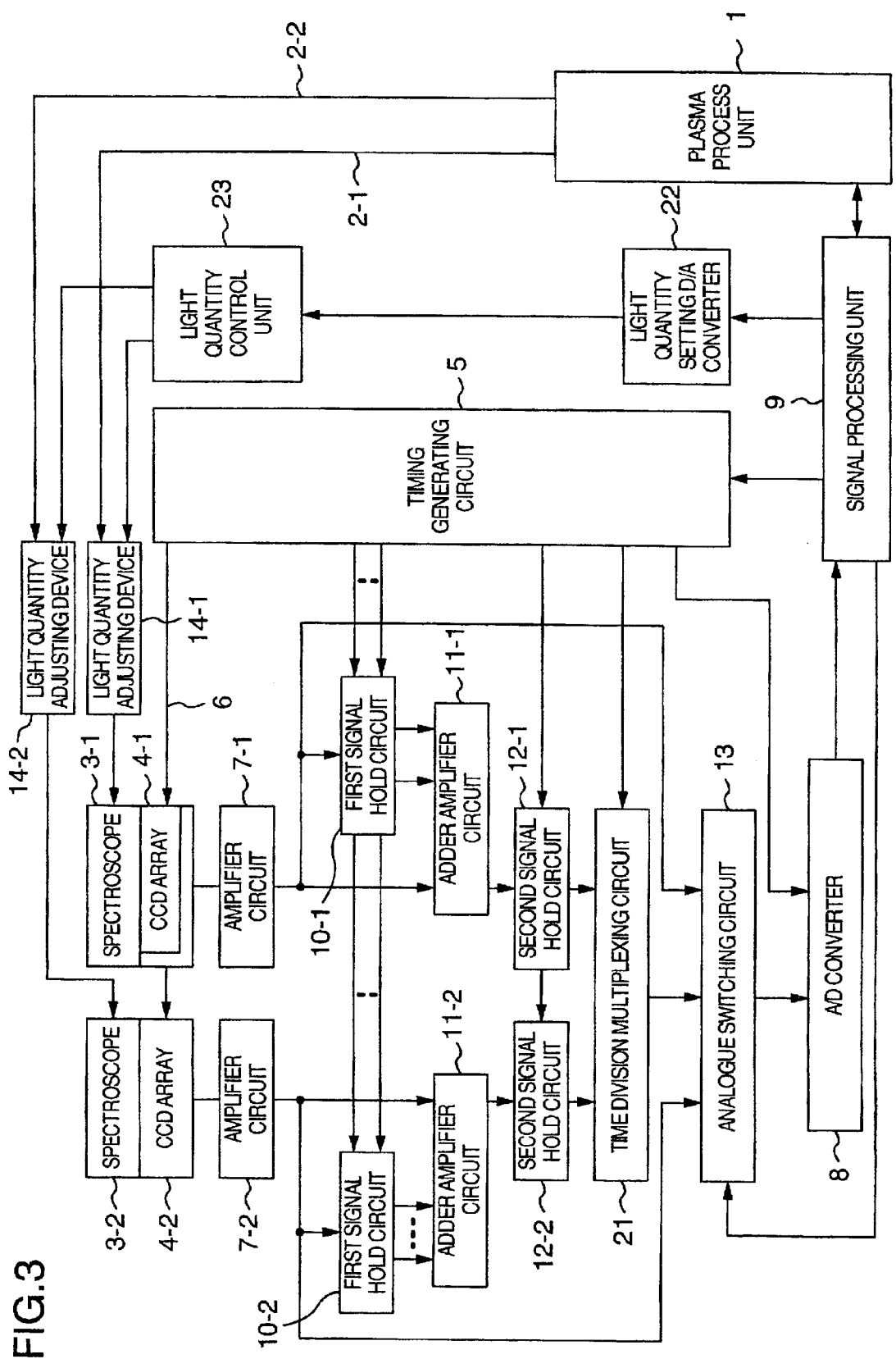
FIG. 3 is a block diagram showing schematically and generally a structure of an emission spectroscopic processing apparatus according to yet another embodiment of the present invention.

FIG. 3 is a block diagram showing schematically and generally a structure of the emission spectroscopic processing apparatus according to yet another embodiment of the present invention. The emission spectroscopic processing apparatus now concerned is designed to analyze simultaneously the emission spectra from two process chambers incorporated in the plasma process unit 1. To this end, the optical fiber, the light quantity adjusting device, the spectroscope, the CCD array, the amplifier circuit, the first signal hold circuit, the adder amplifier circuit and the second signal hold circuit are provided each in a pair, respectively. Namely, they are the optical fibers 2-1 and 2-2, the light quantity adjusting devices 14-1 and 14-2, the spectroscopes 3-1 and 3-2, the CCD arrays 4-1 and 4-2, the amplifier circuits 7-1 and 7-2, the first signal hold circuits 10-1 and 10-2, the adder amplifier circuits 11-1 and 11-2 and the second signal hold circuits 12-1 and 12-2. On the other hand, since the same CCD drive signal 6 is applied in common to the pair of CCD arrays 4-1 and 4-2, the circuit configuration can correspondingly be simplified. Thus, it is sufficient to provide one timing generating circuit 5 and one A/D converter 8.

In the emission spectroscopic processing apparatus according to the instant embodiment of the invention, it is required to digitize two signals with only one A/D converter 8. Accordingly, the outputs of the second signal hold circuits 12-1 and 12-2 are time-serially multiplexed by the time division multiplexing circuit 21, whereon the output of the time division multiplexing circuit 21 is supplied to the A/D converter 8 by way of the analogue switch circuit 13. In this conjunction, it should however be added that the time division multiplexing circuit 21 may be spared by inputting directly the outputs of the second signal hold circuits 12-1 and 12-2 to the analogue switch circuit 13 and performing the A/D conversion while selecting alternately the outputs of the second signal hold circuits 12-1 and 12-2 under the command of the signal processing unit 9. By way of example, in the case where n=16, the amount of the signal deceases by a factor of ⅙. Consequently, with the alternate A/D conversion mentioned above, the A/D conversion speed or rate can be reduced to ⅛ when compared with the single radiation beam input system adopted in the conventional emission spectroscopic processing apparatus.

Further, with the structure of the emission spectroscopic processing apparatus according to the instant embodiment of the invention, it is possible to analyze simultaneously the spectral emissions from four process chambers incorporated in the plasma process unit 1. Also in this case, the A/D conversion speed or rate can be lowered when compared with the single radiation beam input system. Thus, the A/D converter as well as the signal processing unit which are relatively inexpensive can be employed. This presents significant advantage when a plurality of radiation input processings are concurrently performed by resorting to the use of the adder amplifier circuit 11 or adder amplifier circuits 11-1 and 11-2. Moreover, in the case where a measured light and a referenced light both derived from the output of the process unit are employed to be measured by two different CCD arrays, respectively, it is possible to make zero the difference in the sampling time for the data at corresponding wavelength between the CCD arrays mentioned above by driving these CCD arrays in a same timing, whereby arithmetic operations in which the radiation for measurement and the reference light beam of respective wavelengths are used can be performed with high accuracy. In particular, when light which changes frequently such as typified by the plasma radiation is used for measurement reference, respectively, the arrangement for driving the plurality of CCD arrays in a same timing as described above will involve great advantages.

On the other hand, in the case where a plurality of CCD arrays are operated in a same timing as described above, the charge storage times of the individual CCD arrays become naturally same among them, making it difficult to adjust the sensitivity of the CCD arrays individually and independently. Under the circumstances, when the levels of radiations impinging onto a plurality of CCD arrays differ remarkably from one to another in particular, it is preferred to dispose light quantity adjusting devices 14 between the plasma process unit 1 and the optical fibers 2 or alternatively in the optical fibers 2 or alternatively between the optical fibers 2 and the spectroscope 3 while the command issued from the signal processing unit 9 is converted into an analogue quantity by means of a light quantity setting D/A converter 22 with the analogue quantity thus derived being then used for controlling the light quantity adjusting device 14 by way of a light quantity control unit 23, as shown in FIG. 3. Incidentally, as the light quantity adjusting device 14 mentioned above, there may be employed a liquid crystal element whose transmission light quantity varies in dependence on the applied voltage or alternatively a diaphragm mechanism whose optical aperture changes in dependence on the applied voltage or the like.

In the foregoing, description had been made concerning improvement of the S/N ratio and reduction of the data quantity owing to the analogue addition effectuated by using the adder amplifier circuits 11 and others.

In this conjunction, it is noted that the S/N ratio can further be improved by adopting additionally or in combination the digital processing executed by the signal processing unit 9, which will be described below by taking as an example the spectroscopic processing unit shown in FIG. 3 designed for processing two radiation inputs.

It is assumed that the storage time is 25 milliseconds. On this assumption, it is further presumed that for 128 signals of the same channel (same wavelength) inputted every 25 milliseconds, 16 adjacent signals are added together by the adder amplifier circuits 11 to thereby obtain 128 analogue signals for each wavelength (i.e., on a wavelength-by-wavelength basis). The analogue signal is then converted into the digital signal by the A/D converter 8, the output of which is then inputted to the signal processing unit 9. In the signal processing unit 9, the signal for each wavelength inputted every 25 milliseconds is added sixteen times between the adjacent wavelengths and at every sampling. In this way, the signal undergone the average processing over sixteen adjacent wavelengths as well as the signal undergone the average processing through sixteen samplings can be obtained for each of wavelengths. On the basis of these signals, the desired signal processing is carried out, whereby the desired signals which correspond to the two process chambers, respectively, and whose S/N ratios are significantly improved can be obtained every 0.5 millisecond. Furthermore, on the basis of these signals, the end points of the processing in the two process chambers of the plasma process unit 1 can be found individually and independently from each other.

In this case, the S/N ratio can be improved by a factor of about "4" through the analogue addition. Additionally, the S/N ratio can further be improved by a factor of about "4" through the wavelength addition processing executed by the signal processing unit 9. Moreover, the S/N ratio can be improved by a factor of about "4" through addition processing at every sampling point in the signal processing unit. After all, the S/N ratio can be improved by a factor of about "64=4*4*4".

In the case where the S/N ratio of the CCD array 4 is 250 in full scale, the S/N ratio of the radiation signal of 1/64 of the full scale undergoes degradation by about "30=250/√64". However, by effectuating the addition average processing described above, the S/N ratio can be restored to about "1900=30*64". Thus, even a minute change (e.g. 1%) of a low intensity radiation signal corresponding to 1/64 of the full scale can be separated into about 20 levels or gradations.

Although the foregoing description has been made without taking into account the quantization noise involved in the A/D conversion, it is noted that noise can no more be neglected in the case of the minute signal on the order of 1/64 of full scale, because in this case the S/N ratio of the signal will be degraded due to noise or the like disturbance brought about in the A/D conversion. By way of example, considering the case where the conversion to the digital signal is performed by using the A/D converter of 12 bits, noise inclusive of quantization noise and noise in other circuits will amount to ca. 1/3000 to 1/2000 of the full scale. By taking this into consideration, it can be said that the S/N ratio of the light or radiation signal of 1/64 of the full scale will be lowered less than a half of the value mentioned above.

Figure 4:
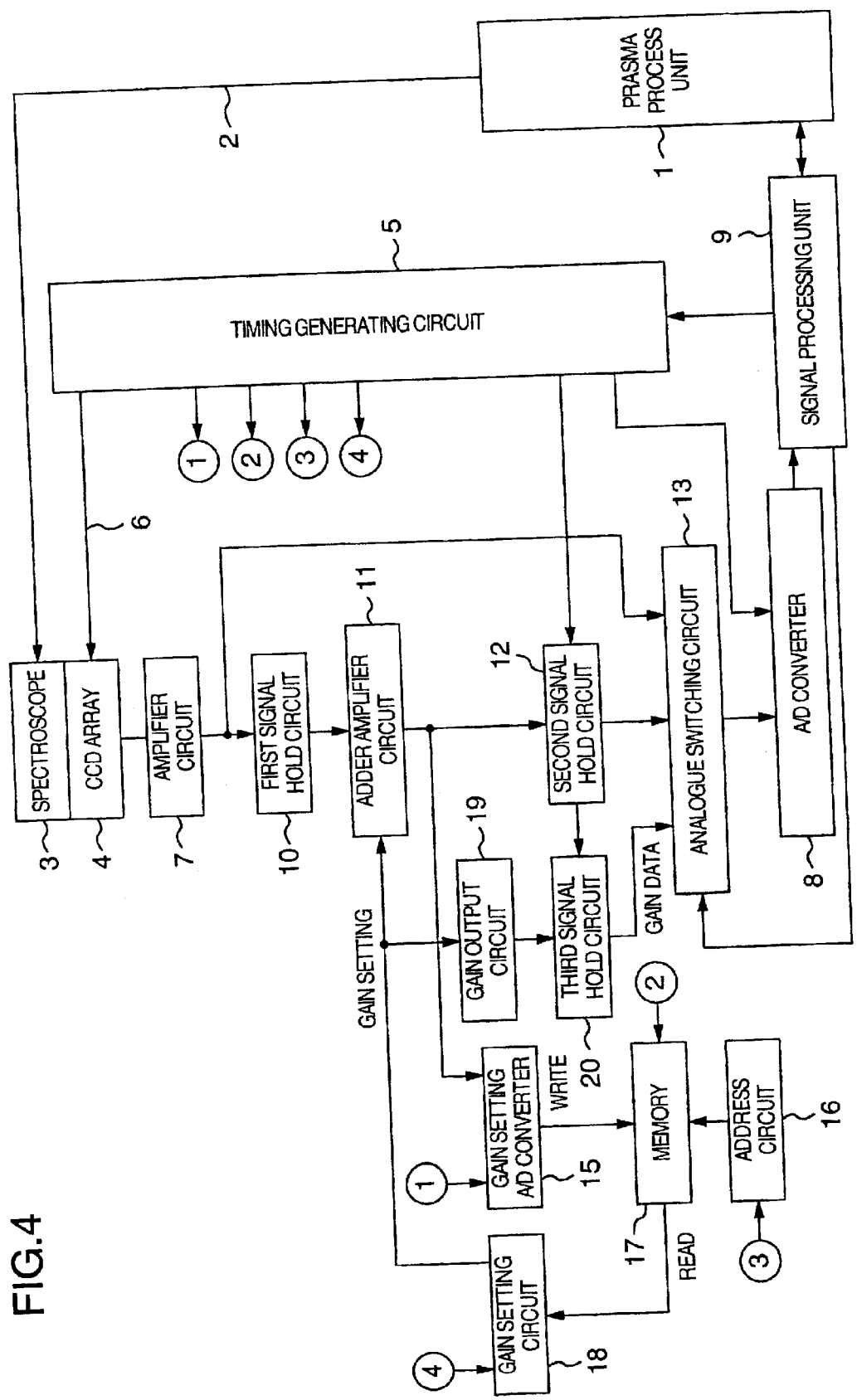
FIG. 4 is a block diagram showing schematically and generally a structure of an emission spectroscopic processing apparatus according to still another embodiment of the present invention.

FIG. 4 is a block diagram showing schematically and generally a structure of the emission spectroscopic processing apparatus according to still another embodiment of the present invention. The spectroscopic processing unit now under consideration is so designed as to change the amplification degree or factor on a wavelength basis upon analogue addition processing. Owing to this arrangement, influences of the quantization noise and the circuit system noise can be reduced.

Upon inputting of the gain setting command for the adder amplifier circuit 11 to the timing generating circuit 5 from the signal processing unit 9, the timing generating circuit 5 responds thereto by starting after the CCD reset timing signal the operation of the gain setting A/D converter 15 (which should preferably be imparted with a sample-and-hold function) in the timing at which the output signal of the adder amplifier circuit 11 (whose gain is set to one (unitary)) is stored in the second signal hold circuit 12. In this conjunction, it should be mentioned that an inexpensive small-size A/D converter capable of outputting a digital signal of less than 8 bits inclusive (e.g. about 4 or 5 bits) may be used as the gain setting A/D converter 15 without any problem. In response to the signal supplied from the timing generating circuit 5, an address corresponding to the wavelength is set in an address circuit 16, and the digital signal outputted from the gain setting A/D converter 15 and indicative of the magnitude of the signal is stored in a memory 17 at a corresponding address thereof.

When the operation described above is performed for one storage time period of the CCD, information concerning the magnitudes of the signals which correspond to 2048/(n+1) wavelengths are stored in the memory 17. In succession, upon inputting of the gain-affixed data output command from the signal processing unit 9 to the timing generating circuit 5, the amplification factor of the adder amplifier circuit 11 is set in correspondence to the information concerning the magnitude of the signal in the memory 17 after the CCD reset timing signal. At that time point, the gain of the adder amplifier circuit 11 is set by way of a gain setting circuit 18 for each of the 2048/(n+1) wavelengths.

The relations between the signal size information mentioned above and the gains of the adder amplifier circuit 11 should preferably be set as follows.

| Signal Size Information (relative to full scale) | | Gain of Adder Amplifier Circuit 11 | |
|---|---|---|---|
| 1) | from 1/4 to 1 | (by) | A times |
| 2) | from 1/8 to 1/4 exclusive | | 2A times |
| 3) | from 1/16 to 1/8 exclusive | | 4A times |
| 4) | from 1/32 to 1/16 exclusive | | 8A times |
| 5) | from 1/32 exclusive | | 16A times |

Incidentally, the value of "A" is ordinarily set to be smaller than "1" (e.g. 1/(n+1), where n represents the number of the first signal hold circuits).

Ordinarily, the spectral signal originating in the plasma emission does not undergo remarkable changes during a single process of specimen treatment. Accordingly, there will usually arise no problem by setting once the gain of the above-mentioned adder amplifier circuit 11 in the stable discharging state at an earlier stage of the process or specimen treatment. However, the signal mentioned above includes a region in which more significant quantization bits are subjected to change due to minute variation of the analogue signal. Such being the circumstances, it is preferred to set the gain of the adder amplifier circuit 11 with a margin so that the adder amplifier circuit 11 is not saturated even when the signal of a wavelength concerned increases (generally by ca. 1.3 times or more) in the course of a single process or specimen treatment.

Parenthetically, the gain setting data for the adder amplifier circuit 11 undergoes conversion to the analogue signal by means of a gain output circuit 19 and a third signal holding circuit 20 to be outputted to the analogue switch circuit 13 time-serially in the same timing as the output of the second signal hold circuit 12. Thus, the gain setting data mentioned above can be read by way of the A/D converter 8 under the command of the signal processing unit 9. As mentioned previously, the gain setting for the adder amplifier circuit 11 may be performed only once in a stable discharging state at an earlier stage of the process or specimen treatment. Accordingly, reading of the gain data mentioned above may be performed only once in the stable discharge state at an earlier stage of the process.

In this manner, the signal processing unit 9 is capable of arithmetically determining in continuation the true value for each of the wavelengths by performing the arithmetic operation on the same wavelengths during the plasma process by using the output data of the third signal holding circuit 20 of the single time-serial gain setting data as set and the output data of the second signal hold circuit 12 outputted time-serially on a storage-time basis during a single process.

At this juncture, it should be mentioned that in the case where only the minute temporal change of the emission spectra during the single process is subjected to the detection, the above-mentioned arithmetic operation carried out by means of the signal processing unit 9 by using the gain setting data is not necessarily required. Further, in conjunction with the instant embodiment of the invention, it has been described that the gain for the adder amplifier circuit 11 is set only once in the stable discharging state at an earlier stage of the process. However, it goes without saying that the gain for the adder amplifier circuit 11 may be set again or repetitively in the course of process or the specimen treatment when the spectrum intensity of a certain wavelength changes significantly in the course of the process being carried out.

Figure 5:
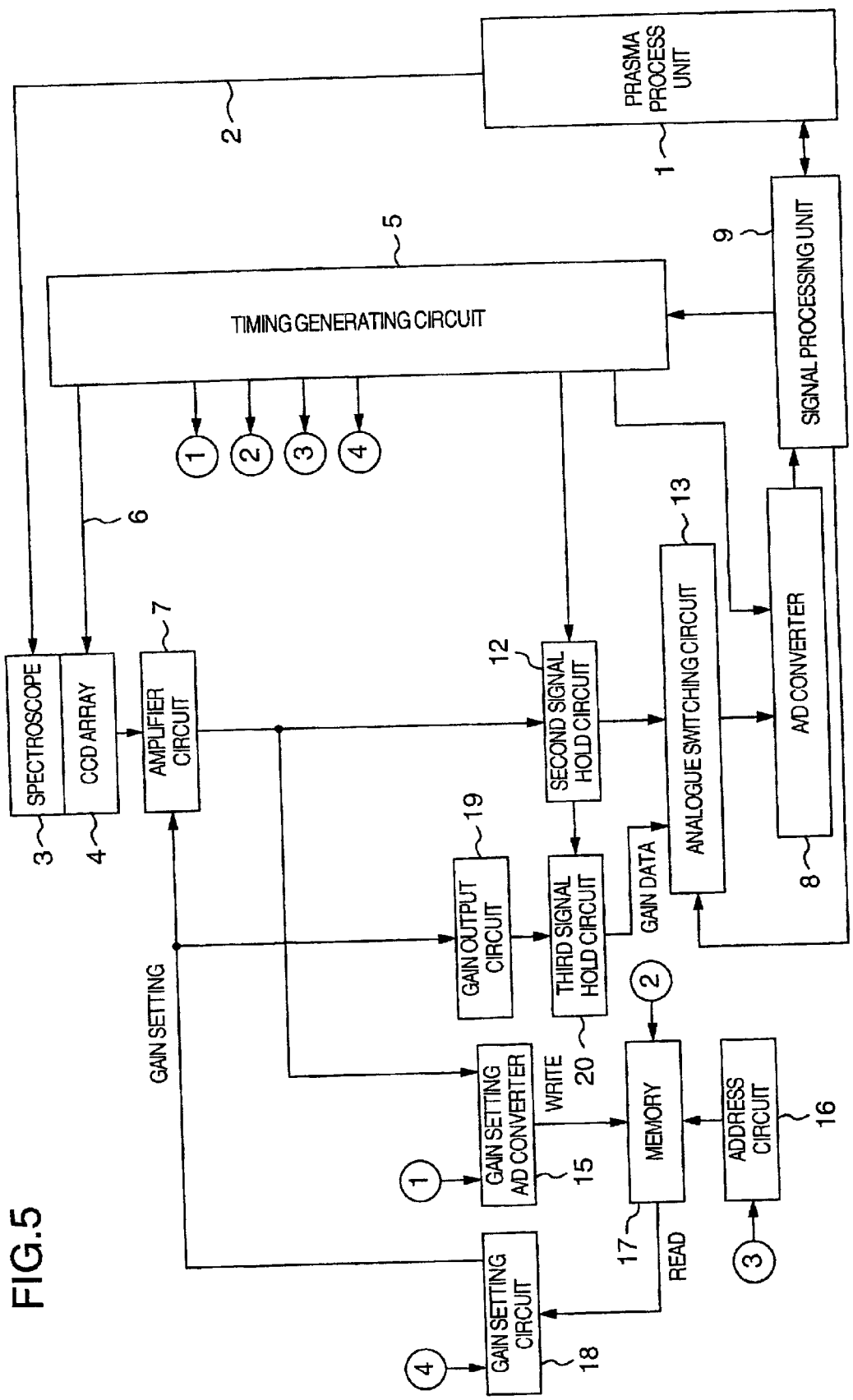
FIG. 5 is a block diagram showing schematically and generally a structure of an emission spectroscopic processing apparatus according to a further embodiment of the present invention.

FIG. 5 is a block diagram showing schematically and generally a structure of the emission spectroscopic processing apparatus according to a further embodiment of the present invention. The spectroscopic processing apparatus according to the instant embodiment of the invention differs from the preceding embodiments in that the signals of different wavelengths are not added together but undergo the A/D conversion after the amplification only. Needless to say, by setting the gain of the amplifier circuit 7 for each of the different wavelengths by means of the gain setting circuit 18, the S/N ratio for the components of low brightness can be improved, the effect of which is however less significant when compared with the emission spectroscopic processing apparatus described previously by reference to FIG. 4 because of low S/N ratio of the analogue signal itself.

In the foregoing, description has been made of typical or preferred embodiments of the emission spectroscopic processing apparatus according to the present invention. By using the processing apparatus, it is possible to detect at earlier stage of the process the minute and high-rate change of the spectral emission in the course of the plasma processing. By way of example, in the case of the plasma processing apparatus employed for gate etching process of a semiconductor device in which the gate-length is not greater than 0.1 μm, the thickness of the base or substrate insulation film subjected to the process is extremely thin as on the order of several nm to 1 nm. Such being the circumstances, the plasma processing step has to be terminated in the state where the above-mentioned film remains in a thickness of several nm to several ten nm before all the etching-subjected film has completely been etched, whereon a succeeding plasma processing step has to be started on the other conditions which can ensure high selectivity ratio relative to the substrate.

For measuring the remaining amount of the etching-subjected film mentioned above, it is necessary to observe or examine interference light from the wafer. However, in the case of this method, the change of light on a wavelength basis is as small as on the order of 0.1% to several %. By contrast, in the case where the spectroscopic processing apparatus described hereinbefore is employed, the S/N ratio of the signal can significantly be improved, and the plasma processing step can be stopped or terminated in correspondence to a high response of one second or less. Thus, the etching process can be performed for the gate length shorter than 0.1 μm inclusive.

On the other hand, in the case where several thousands of wafers are to be treated in succession by the etching process, it is required to know the changes within the process by observing observe the change of light quantity in the state where the resolution of the wavelength is increased. However, high-speed response performance is not necessarily required. In this sort of application, the output signal of the amplifier circuit 7 shown in FIG. 3 is selected by means of the analogue switching circuit 13 to be inputted to the signal processing unit 9 by way of the A/D converter 8. In other words, for this kind of application, resolution of the wavelength is required. Accordingly, the inter-wavelength averaging is not performed but a plurality of sampled data are averaged. Through this procedure, the S/N ratio can be improved in the course of the signal processing.

It is assumed, by way of example, that operation for sampling one data for each wavelength on a 0.5-second basis is carried out for one minute. Then, 120 pieces of data can be sampled for each of the wavelengths. By averaging these sampled data on a wavelength basis, the S/N ratio can be improved by a factor of $\sqrt{120}=10.9$ (i.e., by $\sqrt{120}=10.9$ times). As can now be appreciated, both the detection of minute change which does not require the wavelength resolution but requires the response rate not longer than one second on one hand and the detection of minute change which requires the wavelength resolution with the response rate on the order of several ten seconds on the other hand can be carried out with one and the same apparatus of the structure described hereinbefore by reference to FIG. 3.

Further, the present invention can find application equally to the detection of minute change of the emission component spectra which requires a high-speed response of shorter than 1 second inclusive as well as the monitoring of minute changes of the individual wavelength components of the emission spectra. Furthermore, abnormality of the plasma processing can be prevented in advance by issuing an abnormality signal, an alarm display or terminating a succeeding treatment in the case where the rate of the change should exceed a predetermined value.

As can now be understood from the foregoing, according to the teachings of the present invention incarnated in the illustrated embodiments, it is possible to process speedily and stably the minute changes (not greater than 10%) of the component wavelengths emitted during the plasma processing in the timing within one second inclusive (preferably shorter than 0.5 second inclusive). Besides, the mode in which the minute spectral change in each of the wavelengths emitted in the course of plasma processing is processed stably at a high speed and the mode in which the spectral changes for each of the wavelengths emitted during the plasma processing are determined with high resolution for the adjacent wavelengths, respectively, can be carried out with a single apparatus by changing over the modes mentioned above in dependence on the applications as desired.

Next, description will be made of the digital processing of the light signal obtained from the CCD array. At first, description will be directed to the features or characteristics of the plasma emission in the plasma etching process. In the plasma etching process carried out within a vacuum process chamber, $Cl_2$, HBr, $CF_4$, $C_5F_8$ and the like gases are used as the processing gas (reactive gas), while an Ar-gas is employed for intensifying ionization of the plasma. These gases are decomposed into Cl-, Br-, F-atoms (radicals) exhibiting high reactivity by the plasma. These radical gases react with silicon (Si), polysilicon (Si), oxide film ($SiO_2$), nitride film ($Si_3N_4$), BARC (Back Anti-Reflection Coating), Pt, Fe, SBT ($SrBi_2Ta_2O_9$) and the like which are materials to be etched, to thereby produce reaction products such as SiCl, $SiCl_2$, SiF, SiBr, $C_2$, CO, CN, PtCl, FeCl, TaCl and the like as the etching process proceeds. When the material(s) to be etched becomes unavailable, i.e., when the etching process comes to an end, the reaction products are no more produced and decrease while the radical gases increase.

Thus, intensities of the emission spectra in the course of plasma etching process can be classified into (1) spectra due to the reaction products which decrease at the time point when the etching of the materials to be etched is terminated, (2) spectra due to the radicals which increase at the end point of the etching, and (3) spectra due to materials irrelevant to the etching reaction and undergoing no change before and after the end of the etching (i.e., around the end point of etching).

In the method of determining the end point based on the plasma emission, time-dependent change of the emission intensity of a specific spectrum wavelength (e.g. spectrum due to the reaction product) is used among the emission spectra mentioned above. However, since the emission spectrum signals derived from the output of the CCD array contain noise components in dependence on the signal intensity, as described hereinbefore, the noise components make it difficult to detect the end point of the etching process with the method in which the differential waveform of the emission spectrum signal is made use of for detecting the end point of the etching process.

Figure 6:
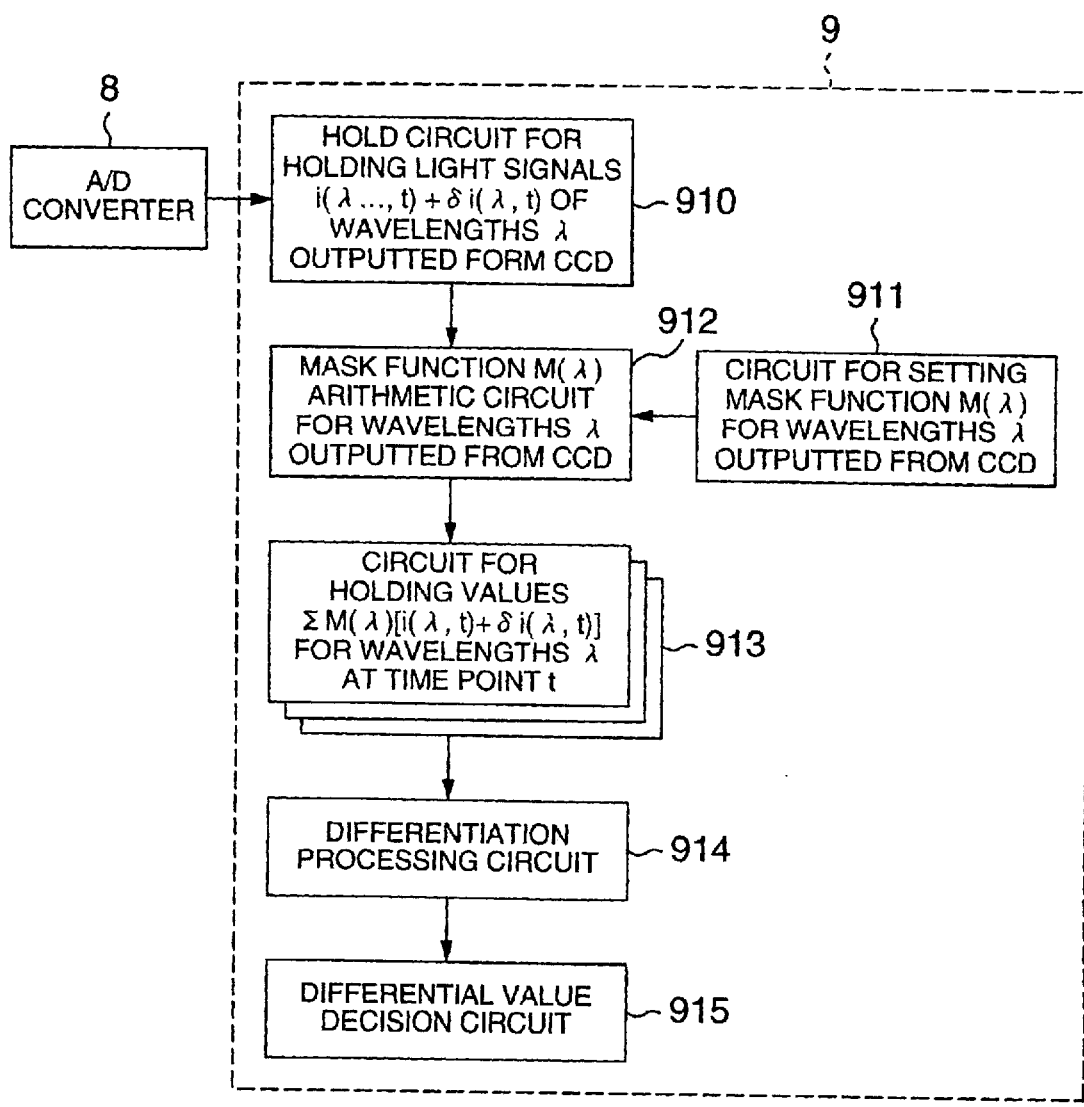
FIG. 6 is a block diagram showing schematically and generally a structure of a signal processing unit incorporated in an emission spectroscopic processing apparatus according to an embodiment of the present invention.
Figure 7:
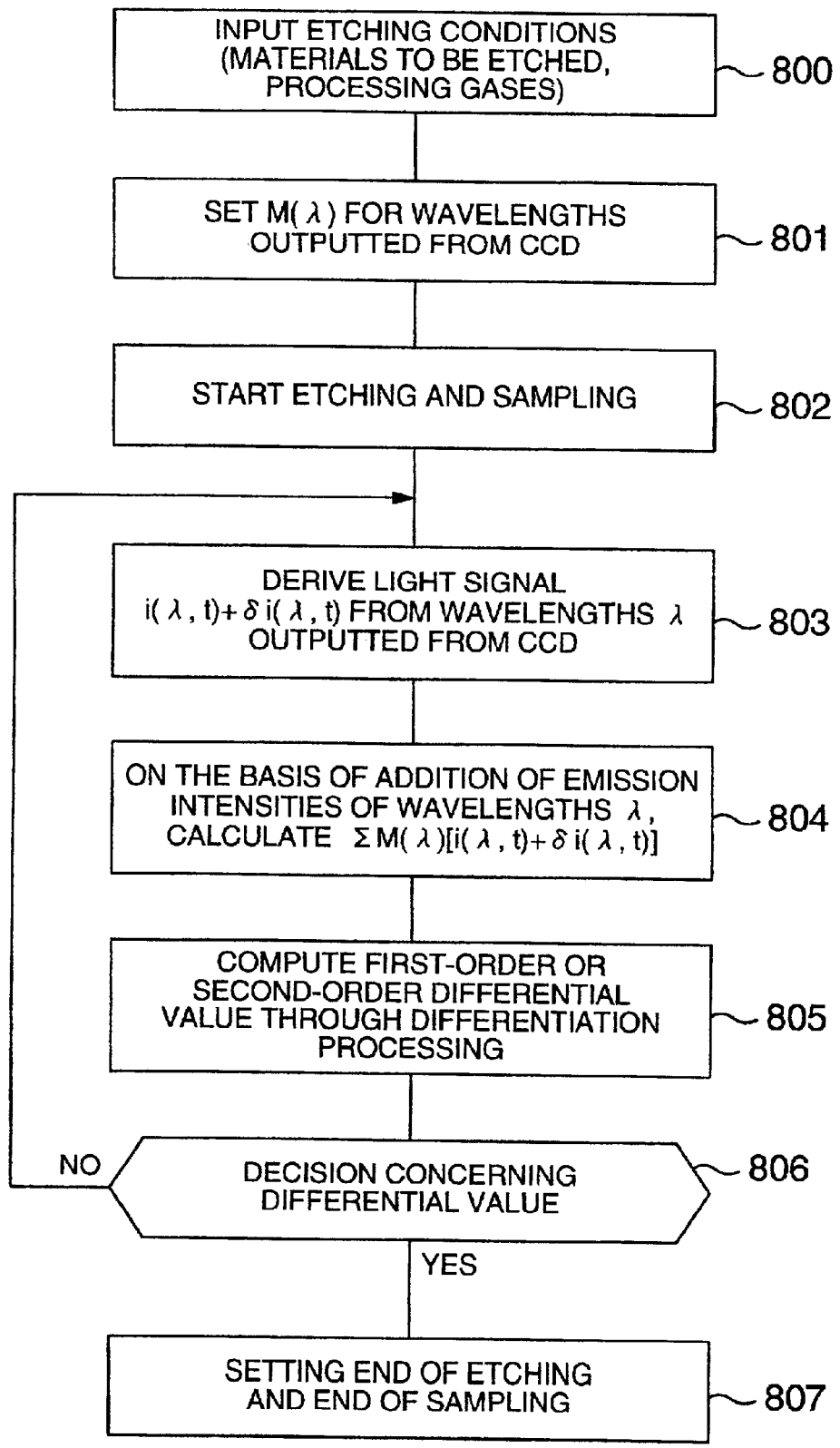
FIG. 7 is a flow chart for illustrating a digital signal processing procedure according to an embodiment of the present invention.

In the following, referring to FIGS. 6 and 7, exemplary embodiments of the present invention designed for eliminating the noise components will be described. It is assumed that the digitized signal resulting from digitization of the emission spectrum signal of wavelength λ derived from the output of the CCD array at a time point t by means of the A/D converter 8 is expressed in terms of a light signal component i(λ, t) and a noise component δi(λ, t). In this conjunction, the noise components δi(λ, t) are attributable to electrical noise in the CCD array and fluctuation noise of light. The emission spectrum signal i(λ, t)+δi(λ, t) is temporarily saved in a digitized data hold circuit 910 incorporated in the signal processing unit 9 mentioned hereinbefore, whereon the above-mentioned emission spectrum signal i(λ, t)+δi(λ, t) and a mask function M(λ) are added together for all the wavelengths λ measured by using preset values of an emission spectrum classifying mask function M(λ) circuitry 911 by means of an arithmetic circuitry 912. The integrated or sum value ΣM(λ)[i(λ, t)+δi(λ, t)] for λ is stored in a sum value hold circuit 913, whereon time-dependent differential value of the emission intensity is determined by means of a differentiation processing circuit 914. By making use of this time-dependent differential value of the emission intensity, the end point of the etching process is determined by a differential value decision circuit 915. A processing flow to this end is illustrated in FIG. 7. Referring to the figure, the mask function M(λ) is set for the CCD wavelengths in a step 801 by inputting the etching conditions such as of materials to be etched and the processing gases (step 800). Subsequently, upon starting of the etching process, sampling of the light signal outputted from the CCD array is started (step 802), whereby light signals i(λ, t)+δi(λ, t) for the individual wavelengths λ derived from the output of the CCD are acquired (step 803). In succession, the integrated or sum value ΣM(λ)[i(λ, t)+δi(λ, t)] of the light signal and the mask function M(λ) for all the wavelengths λ is arithmetically determined (step 804). On the basis of this integrated or sum value ΣM(λ)[i(λ, t)+δi(λ, t)], the time-dependent differential value of the emission intensity at the time point t is determined (step 805). By comparing this time-dependent differential value with a preset differential value as reference for decision (step 806), the light signal i(λ, t)+δi(λ, t) is again acquired (step 803) or alternatively the etching process or the light signal sampling is terminated (step 807). In conjunction with the integrated or sum value of λ, i.e., ΣM(λ)[i(λ, t)+δi(λ, t)], it is to be noted that the term Σ[δi(λ, t)] represents random noise. Consequently, the sum value resulting from the summation of a large number of wavelengths λ approaches to zero. In other words, through this summation process, there arises the possibility of noise elimination.

Next, description will be made as to the method for classification of the emission spectra. For determining discriminatively whether the emission spectrum of wavelength λ derived from the output of the CCD array is the light signal which decreases around the end point of the plasma etching process or alternatively the light signal which increases or alternatively the light signal which undergoes no change, there can be adopted the methods described below.

(1) A database of the reaction products of the reactive gases and the materials to be etched is prepared in advance on the basis of a spectrum library (see literature: CRC Handbook of Chemistry and Physics, David R. Lide, CRC Press, R. W. Pearse and A. G. Gaydon, "THE IDENTIFICATION OF MOLECULAR SPECTRA", John Wiley & Sons, Inc., 1976), and by referencing the database, the wavelengths belonging to the reactive gases are classified as the wavelengths increasing before and after (i.e., around) the end point of the etching process while the wavelengths belonging to the reaction products are wavelengths, around, the end point of the etching process with the other wavelengths being classified as those irrelevant to the reaction and undergoing essentially no time-dependent change.

(2) A sample wafer processing (etching process of wafers containing same species of the materials to be etched is performed. In conjunction with the time-dependent changes of the emission spectra in the etching process, differentiation processing is performed for all the wavelengths, whereon the wavelengths are classified on the basis of the first-order differential values around the etching end point. As the differentiation processing method to this end, a method described in Japanese Patent Application Laid-Open Publication No. 228397/2000 (JP-A-12-228397) may be adopted. More specifically, the wavelength for which the first-order differential value is negative (minus) is classified as the wavelength which decreases around the etching end point (i.e., wavelength attributable to the reaction product), the wavelength for which the first-order differential value is positive (plus) is classified as the wavelength which increases around the etching end point (i.e., wavelength attributable to the radical), while the wavelengths whose first-order differential value is zero is classified as the wavelength which undergoes no change around the end point of the etching process (i.e., the wavelength irrelevant to the reaction).

(3) A sample wafer processing (etching process of wafers containing same species of the materials to be etched) is performed. In conjunction with the time-dependent changes of the emission spectra for all the wavelengths in the etching process, the main component analysis is performed to determine spectra of the individual components, whereon the wavelengths are classified on the basis of the spectrum values of the individual components. Concerning the analysis of the principal components, reference is to be made to S. Minami: "WAVEFORM DATA PROCESSING FOR SCIENTIFIC MEASUREMENTS" CQ publication company of Japan, pp. 220–226 (1986) and K. Sasaki, S. Kawata and S. Minami, "ESTIMATION OF COMPONENT SPECTRAL CURVES FROM UNKNOWN MIXTURE SPECTRA", Appl. Opt. Vol. 23, pp. 1955–1959 (1984). The method disclosed in these references can be adopted in carrying out the present invention. The wavelengths are classified on the basis of the spectrum values of given components determined by the principal component analysis. By way of example, the wavelength for which a spectrum value of a certain component is negative is classified as the wavelength which decreases around the etching end point (i.e., wavelength attributable to the reaction product), the wavelength for which the spectrum value is positive is classified as the wavelength which increases around the etching end point (i.e., wavelength attributable to the radical), while the wavelength whose spectrum value is zero is classified as the wavelength which undergoes no change around the end point of the etching (i.e., the wavelength irrelevant to the reaction). It should however be noted in conjunction with the methods described above that the positive spectrum value is not always attributable to the reaction product and that negative spectrum value is not always that of the radical either.

In order to discriminatively identify three groups resulting from the classification through the procedures described above, operator M(λ) is introduced. By way of example, for the wavelength λ whose intensity increases around the etching end point is assigned with the operator M(λ)=−1, while the wavelength λ whose intensity decreases around the etching end point is assigned with the operator M(λ)=1. Further, the wavelength λ whose intensity undergoes no change around the etching end point is assigned with the operator M(λ)=1.

Figure 8:
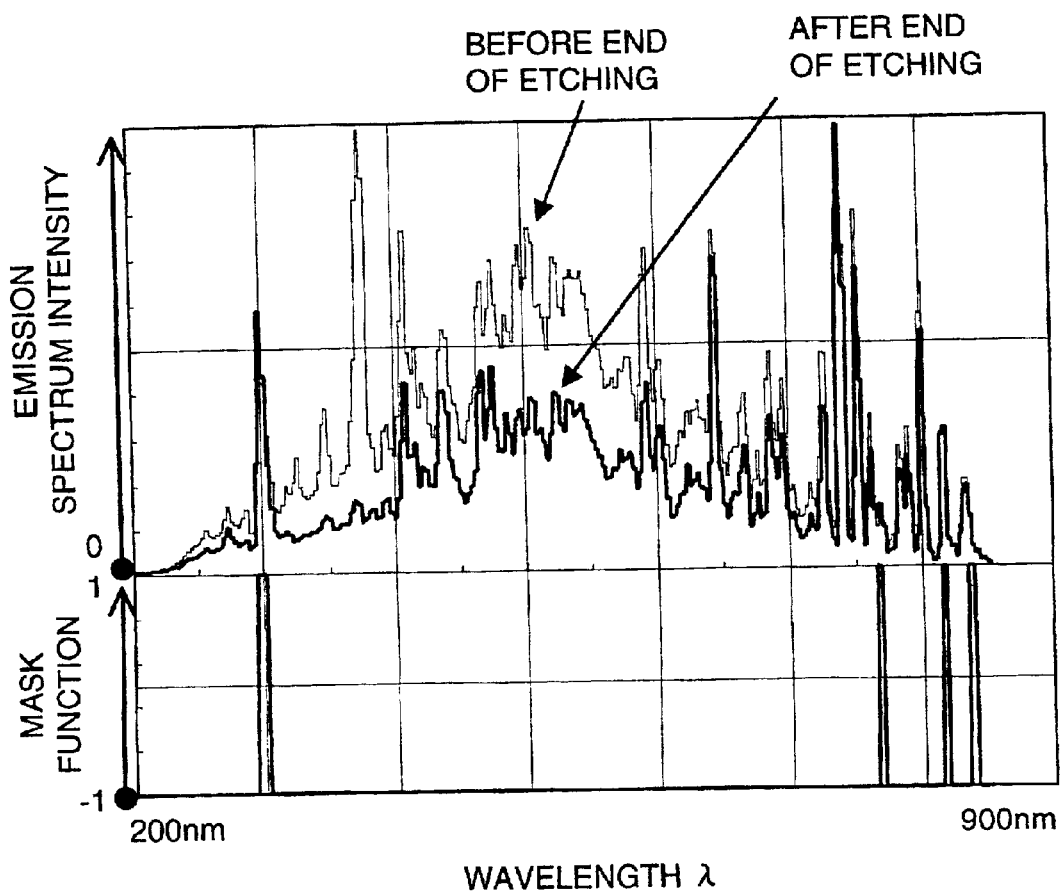
FIG. 8 is a view showing, by way of example, relations between intensities and wavelengths of emission spectra together with a mask function in an emission spectroscopic processing apparatus according to an embodiment of the present invention.
Figure 9:
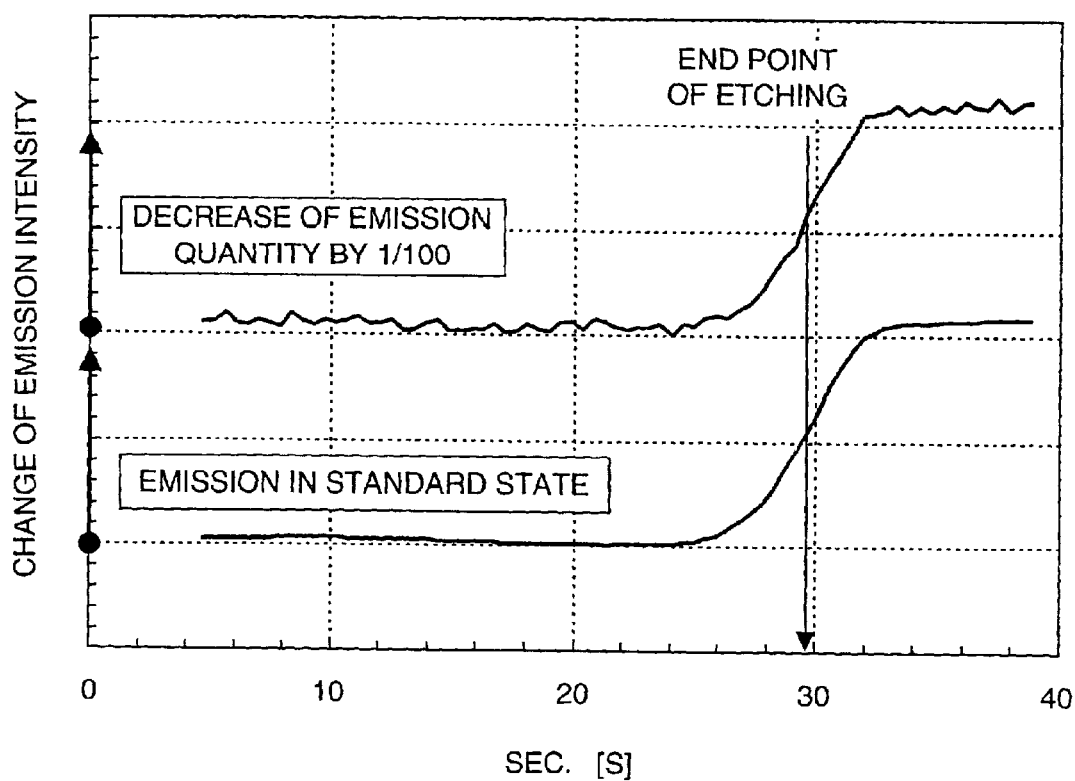
FIG. 9 is a view for graphically illustrating, by way of example, time-dependent changes of intensities of emission spectra.

FIGS. 8 and 9 show results of BARC (Back Anti-Reflection Coating) etching process to which the teaching of the invention incarnated in the instant embodiment is applied. The etching process gas is a gas mixture of HBr, $CF_4$, $O_2$ and Ar. In FIG. 8, there are graphically illustrated, by way of example only, the emission spectra before and after the BARC etching, respectively. As can be seen in FIG. 8, many emission spectra of CN, CO, $C_2$ and others which are reaction products in the BARC process decrease around the time point at which the etching is ended, while emission spectra of OH and O increase. By performing differentiation processing on the time-dependent change (i.e., change as a function of time lapse), the time-dependent change behaviors of the emission spectra are classified to thereby determine the mask function $M(\lambda)$ shown in the figure. The sum $\Sigma M(\lambda)[i(\lambda, t)+\delta i(\lambda, t)]$ determined concerning the wavelength $\lambda$ by using the mask function $M(\lambda)$ is illustrated in FIG. 9. Referring to this figure, in the standard state, the mean value of the emission spectrum intensities is about 1220 counts, while in the state where the emission quantity decreases by $\frac{1}{100}$, the squeezed mean value of the emission spectrum intensities is about 12.2 counts. As can be seen, according to the teachings of the present invention, the time-dependent change of the emission intensity can be determined with sufficiently high accuracy even in the state where the emission quantity has decreased by $\frac{1}{100}$ because noise components can sufficiently be eliminated.

Figure 10:
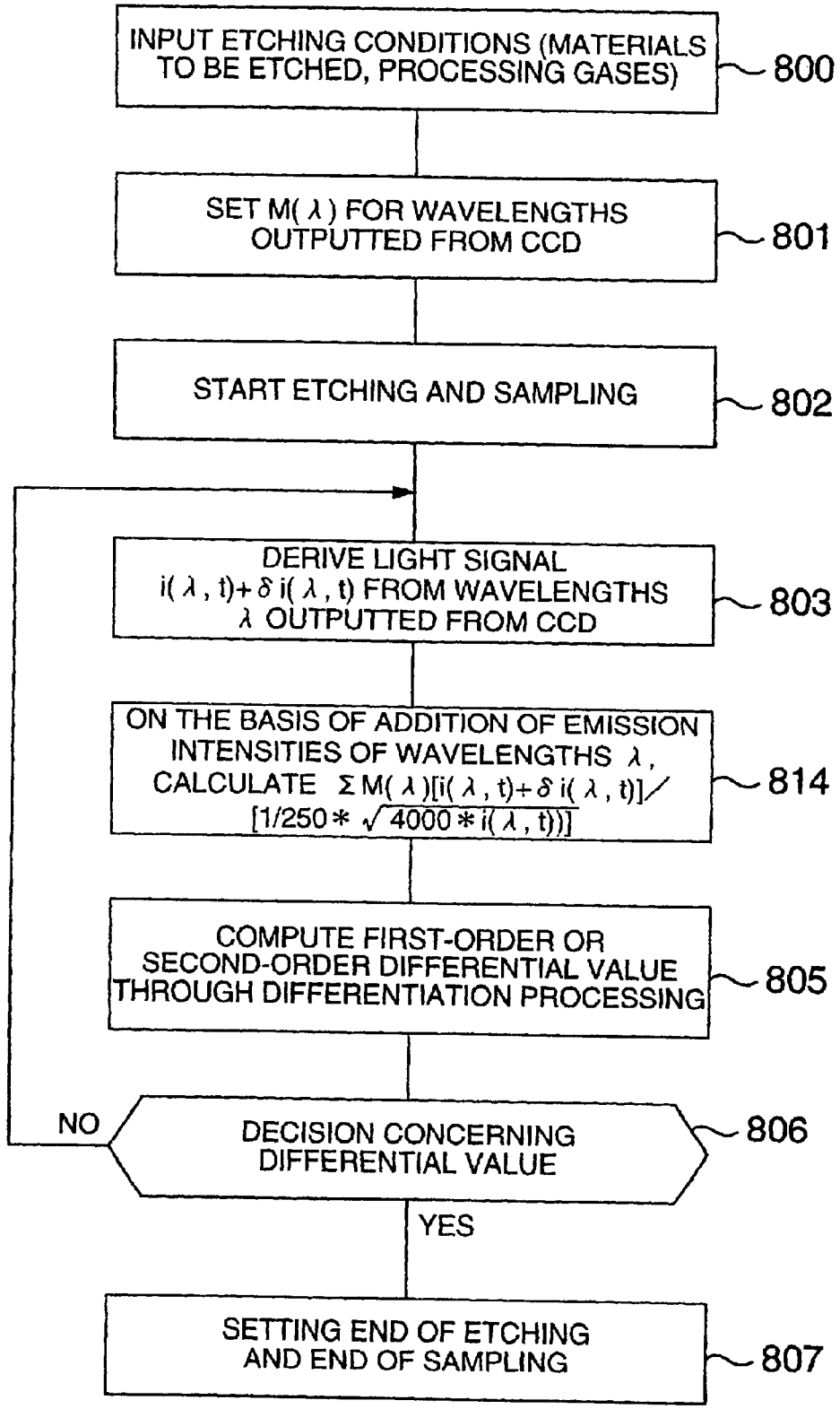
FIG. 10 is a flow chart for illustrating a digital signal processing procedure according to a further embodiment of the present invention.

Next, description will be made of an embodiment of the invention in which the trend of the noise components $\delta i(\lambda, t)$ outputted from the CCD array being in reverse proportion to the intensity of the light signal component $i(\lambda)$ is taken into consideration. In the experiments as conducted, a CCD array commercially available from Sony Ltd. under the commercial name "ILX 511" was used. The S/N ratio of this CCD can be expressed as ca. $250\sqrt{(i(\lambda)/4000)}$, while the noise component can be given by $\delta i(\lambda, t) = \frac{1}{250} \cdot \sqrt{(4000 \cdot i(\lambda, t))}$. For example, when $i(\lambda)=4000$, noise can be given by $\delta i(\lambda, t)=16$ (S/N=250). On the other hand, for $i(\lambda)=10$, $\delta i(\lambda, t)=0.8$ (S/N=12.5). When integration or summation operation is performed simply for $\lambda$, contribution to the S/N ratio of the emission quantity is neglected. This can be taken into account by standardizing the integrating or summing operation $\Sigma M(\lambda)[i(\lambda, t)+\delta i(\lambda, t)]$ performed on $\lambda$ with the noise component $\delta i(\lambda, t)$. In other words, for $\lambda$ shown in FIG. 8, the sum 804 may be determined as $\Sigma M(\lambda)[i(\lambda, t)+\delta i(\lambda, t)]/[\frac{1}{250} \cdot \sqrt{(4000 \cdot i(\lambda, t))}]$ (see a step 814 in the flow chart shown in FIG. 10).

Figure 11:
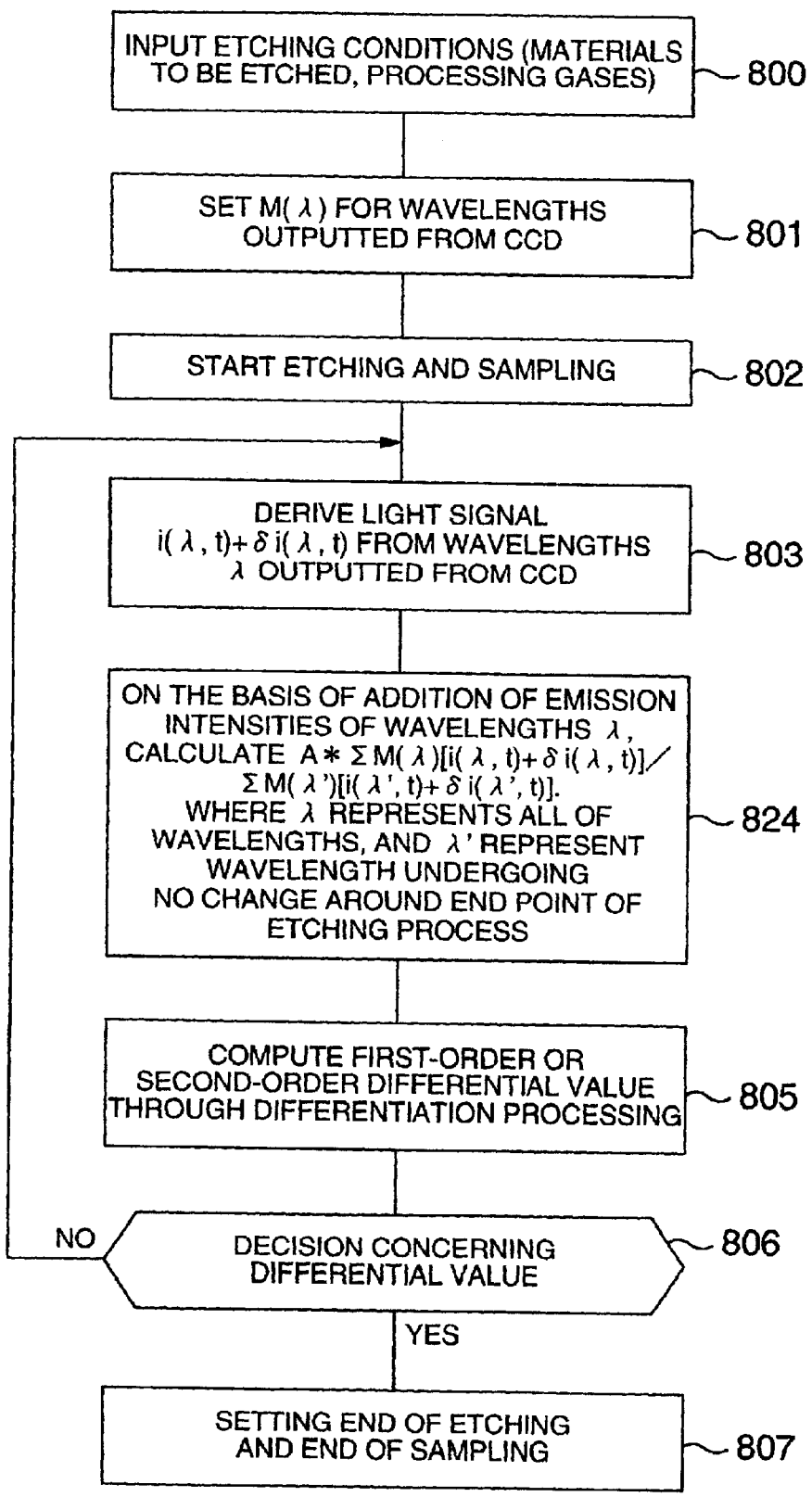
FIG. 11 is a flow chart for illustrating a digital signal processing procedure according to a still further embodiment of the present invention.

Finally, description will be directed to an embodiment of the invention which is so arranged as to cancel out fluctuations or changes such as those ascribable to abnormal discharge of the plasma emission, if it occurs. The value of the mask function $M(\lambda)$ mentioned previously is, for example, set as follows. For the wavelength $\lambda$ for which the emission intensity increases around the end point of the etching process is set equal to "2", i.e., $M(\lambda)=2$. On the other hand, for the wavelength $\lambda$ of which emission intensity decreases around the end point of the etching process is set to "−2", i.e., $M(\lambda)=-2$. Further, for the wavelength $\lambda$ whose emission intensity undergoes substantially no change is set to "1", i.e., $M(\lambda)=$"1". In this way, the wavelength ($\lambda$) for which emission intensity undergoes no change around the end point of the etching process can be distinguished from the other wavelengths, and the light signal of this wavelength $\lambda$ can be used for standardization of the summation of $\lambda$, i.e., $\Sigma M(\lambda)[i(\lambda, t)+\delta i(\lambda, t)]$. In other words, summing $A \cdot \Sigma M(\lambda)[i(\lambda, t)+\delta i(\lambda, t)]/\Sigma M(\lambda')[i(\lambda', t)+\delta i(\lambda', t)]$ is arithmetically determined. In this conjunction, the term $\Sigma M(\lambda')[i(\lambda', t)+\delta i(\lambda', t)]$ represent the sum value for the wavelength $\lambda'$ whose emission intensity does not change around the end point of the etching. Further, the coefficient integration represents the value of $\Sigma M(\lambda')[i(\lambda', t)+\delta i(\lambda', t)]/\Sigma M(\lambda)[i(\lambda, t)+\delta i(\lambda, t)]$ at an appropriate time point to after the plasma etching process has been started. Through this standardization or normalization processing (see step 824 in the flow chart of FIG. 11), it is possible to cancel out fluctuations of emission spectra possibly brought about by abnormal electric discharge, and thus determination as to the end point of the etching process can be made with high accuracy and reliability.

Further, in the case where the wavelength for which emission intensity does not change around the end point of the etching process is absent, then the integration or summation value for the wavelength whose emission intensity increases around the end point of etching can be used for the standardization or normalization substantially to the similar advantageous effect. In other wards, addition of $\lambda'$ in the summation $A \cdot \Sigma M(\lambda)[i(\lambda, t)+\delta i(\lambda, t)]/\Sigma M(\lambda')[i(\lambda', t)+\delta i(\lambda', t)]$ may be performed for the wavelength $\lambda$ of which emission intensity increases around the end point of the etching process.

As is apparent from the above, the present invention has provided the emission spectroscopic processing apparatus which is capable of detecting high-rate minute changes of emission spectra with improved reproducibility.

It should be further understood by those skilled in the art that the foregoing description has been made on embodiments of the invention and that various changes and modifications may be made in the invention without departing from the spirit of the invention and the scope of the appended claims.

What is claimed is:

1. An emission spectroscopic processing apparatus, comprising:

a spectroscope for spectrally separating input light emitted from a process unit into component spectra;

a light receiving unit including a series of light receiving elements for detecting light quantities of said component spectra on a wavelength basis;

a first signal hold unit for holding sequentially each of detection signals outputted from a subset of adjacent light receiving elements contained in said series of light receiving elements during a first period;

an adder unit for adding together the detection signals of adjacent light receiving elements of said light receiving unit inclusive of said held detection signals of said subset of the adjacent light receiving elements;

a second signal hold unit for holding sequentially sum outputs of said adder unit; and a signal processing unit for determining a state of said process unit on the basis of the output of said second signal hold unit.

2. An emission spectroscopic processing apparatus according to claim 1, wherein said first signal hold unit includes
a first stage of signal hold part for holding sequentially the detection signals outputted from a subset of adjacent light receiving elements in said series of light receiving element for a first period, respectively; and
a second stage of signal hold part for holding sequentially sum outputs of said first stage of signal hold part sequentially for a second period longer than said first period.

3. An emission spectroscopic processing apparatus according to claim 1, wherein said signal processing unit includes
selecting means for inputting either the output of said adder unit or the detection signal outputted from each of said adjacent light receiving elements of said light receiving unit.

4. An emission spectroscopic processing apparatus according to claim 1,
   wherein said first signal hold unit is so designed as to hold detection signals of said input light amplified with ratios differing from one to another of plural adjacent light receiving elements of said light receiving unit.

5. An emission spectroscopic processing apparatus according to claim 1,
   said process unit being a plasma processing apparatus,
   wherein said emission spectroscopic processing apparatus is designed to stop etching process of said plasma processing apparatus on the basis of a sum output of said adder unit.

* * * * *